United States Patent [19]

Gagnon et al.

[11] 4,015,121
[45] Mar. 29, 1977

[54] CATALSIMETER WITH TIME MEASURING CIRCUITRY FOR DETERMINING REACTANT CONCENTRATION LEVEL

[75] Inventors: Marcel Gagnon, St. Lambert; Michel Baril, Pointe Claire; Francois-Gros D'Aillon, Rosemere; Claude Savoie, St. Basil Le Grand, all of Canada

[73] Assignee: Allca Instruments Co. Ltd., Montreal, Canada

[22] Filed: July 15, 1975

[21] Appl. No.: 596,166

Related U.S. Application Data

[62] Division of Ser. No. 487,615, July 11, 1974, Pat. No. 3,948,730.

[52] U.S. Cl. .............................. 250/221; 250/564; 250/575; 250/573
[51] Int. Cl.² ................. G01D 21/04; G01N 21/26; G01N 21/28
[58] Field of Search ............... 195/103.5 R; 356/28; 250/574, 575, 576, 577, 221, 564–573; 324/175

[56] References Cited
UNITED STATES PATENTS

| | | | |
|---|---|---|---|
| 1,950,273 | 3/1934 | Speakman | 250/221 |
| 2,888,573 | 5/1959 | Kavanagh | 250/575 |
| 3,590,256 | 6/1971 | Neeff | 250/573 |
| 3,764,479 | 10/1973 | Bergeron et al. | 195/103.5 R |
| 3,843,265 | 10/1974 | Egli et al. | 250/565 |

*Primary Examiner*—Alfred E. Smith
*Assistant Examiner*—David K. Moore
*Attorney, Agent, or Firm*—Pennie & Edmonds

[57] ABSTRACT

This invention relates to an apparatus and a method for determining the concentration of a first reactant in a medium. A disc is saturated with a solution containing the first reactant and immersed into a second reactant fluid. A chemical reaction occurs between the first and second reactants to produce a gas which is trapped by the disc. The disc is buoyed to the surface of the second reactant fluid by the gas produced. The process is electronically timed using photocells to start and stop an electronic clock and a digital display displays the time elapsed in tenths of seconds.

12 Claims, 4 Drawing Figures

CATALSIMETER WITH TIME MEASURING CIRCUITRY FOR DETERMINING REACTANT CONCENTRATION LEVEL

The present invention is a division of application Ser. No. 487,615, filed July 11, 1974, and now U.S. Pat. No. 3,948,730, issued on Apr. 6, 1976.

INTRODUCTION AND GENERAL DISCUSSION

This invention relates to an apparatus and a method for determining the concentration of a first reactant in a medium. In particular, the present invention provides a method and apparatus for determining the concentration of a catalase enzyme in a medium.

In the determination of the concentration of a first reactant in a medium, the medium can be immersed into a fluid containing a second reactant in a known concentration which reacts with the first reactant to produce a gas. If the chemical composition of the reacting fluid is known, then the rate of gas production can be used to calculate the desired concentration of first reactant using, for example, the Gagnon-Hunting method. This rate can be measured electronically if a gas-trapping object of a known size is saturated with the medium containing the first reactant and then immersed into the fluid containing the second reactant. The gas trapped by the gas-trapping object will reduce the weight of the gas-trapping object by the resultant buoyant force, and the rate of increase of the buoyant force is proportional to the rate of gas production.

If the gas-trapping object sinks in the fluid when not filled with the gas to be produced, and also rises to the surface of the fluid when partially filled with the trapped gas produced, the time taken for the object to sink and rise to the surface of the fluid can be measured electronically. This time will be proportional to the buoyant force acting on the gas-trapping object, and hence proportional to the rate of gas production in the reaction, and therefore proportional to the concentration of the first reactant in the medium.

In the particular case where the concentration of the catalase enzyme is to be determined, the second reactant is $H_2O_2$. $H_2O_2$ is typically placed in the fluid at a required concentration by volume. The gas-trapping object can be conveniently a disc shaped piece of filter paper of a known size.

Occasionally, when the disc of filter paper is dropped into the $H_2O_2$, it does not immediately sink but flips over and rises to the surface of the fluid almost immediately after it is dropped. This action causes light beams from the photocell detector to be broken twice when the disc enters the fluid, hence starting the clock and stopping it immediately afterwards. This situation was corrected by an appropriate control circuit which will ignore a signal from the photodetector unless that signal is received after a predetermined time has elapsed. This allows the disc to flip over without affecting the electronic clock.

STATEMENT OF INVENTION

In accordance with the present invention, there is provided a method of measuring the concentration of a first reactant in a medium by reacting it with a second reactant fluid of a predetermined concentration to produce a gas, said method comprising the steps of:

a. saturating a gas-trapping object of known weight with said medium containing said first reactant;

b. placing said gas-trapping object into an open container which contains, to a predetermined depth, a quantity of said fluid; and c. measuring electronically the time taken for said gas-trapping object to sink into said fluid, and the time taken to produce a quantity of gas sufficient to buoy said gas-trapping object to the surface of said fluid, wherein the time taken for said gas-trapping object to sink into said fluid and to be buoyed to the surface by said gas is proportional to the concentration of said first reactant in said medium.

In accordance with the present invention, there is also provided a circuit for electronically measuring and displaying the time taken for a gas-trapping object saturated with a medium containing a first reactant to sink and rise to the surface of a fluid containing a second reactant at a predetermined concentration in a container due to the reaction of said first and second reactants, said circuit comprising:

a. photo-detector means for producing a start pulse when said gas-trapping object enters said fluid and a stop pulse when said gas-trapping oject rises to the surface of said fluid; and b. clock means operatively associated with said photo-detector means for displaying elapsed time between the receipt of said start pulse and said stop pulse, said elapsed time being proportional to the concentration of said first reactant in said medium.

DESCRIPTION OF THE DRAWINGS

The invention will now be described with reference to the accompanying drawings, in which.

DETAILED DESCRIPTION

Figure 1:
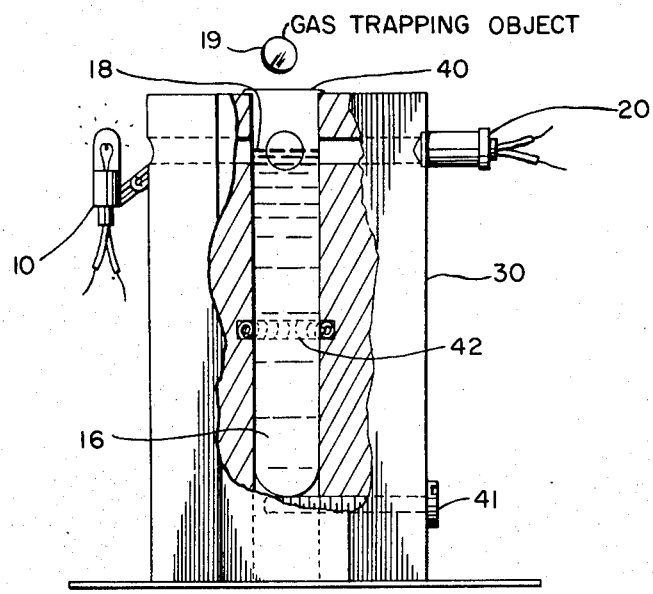
FIG. 1 is a side elevation of a part of a particular embodiment according to the present invention.
Figure 2:
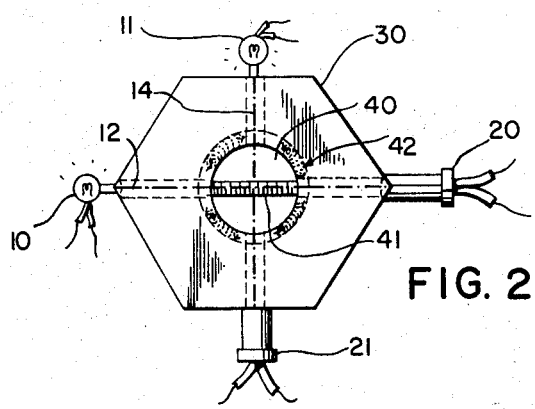
FIG. 2 is a top plan view of that part of the embodiment shown in FIG. 1.

Referring to FIGS. 1 and 2, the apparatus shown is comprised of lamps 10 and 11 affixed to and oriented 90° about a hollow container 30. Lamps 10 and 11 provide orthogonally oriented light beams 12 and 14 which impinge on photoresistors 20 and 21 respectively. These photoresistors are attached to opposite sides of the container from the lamps. Normally, test tube 40 will rest in the container on test-tube stopper 41 and will be held in place by test tube spring 42 which encircles the test tube. When in use, test tube 40 will be partially filled with a reactant fluid 16 of known chemical composition. The height of the fluid in the test tube is such as to provide a surface 18 which will correspond to a plane defined by the light beams which enter the photoresistors, so that any object entering or floating on the surface of the fluid will interrupt one or both of the light beams. Two orthogonally oriented lamp and photoresistor combinations are used to ensure that at least one of the beams 12 or 14 will be interrupted regardless of the position that the object enters the fluid or floats on the surface 18 of the fluid 16.

A gas-trapping element 19 (FIG. 1), for example a disc of filter paper of known dimension, is immersed in a fluid medium containing the first reactant, the concentration of which is to be determined. The disc, so conditioned is then dropped into the test tube 40, breaking one or both of the light beams 12 and 14 thereby starting an electronic counter which will be described in detail below, and sinks into the fluid column. The first reactant reacts with the reactant fluid 16 to produce a gas. The disc traps the gas so produced, becoming buoyant and eventually floating to the surface 18, breaking one or both of the light beams 12 and 14, thereby stopping the counter. The timed reading of the counter will be proportional to the concentration of the first reactant in the medium.

Figure 3:
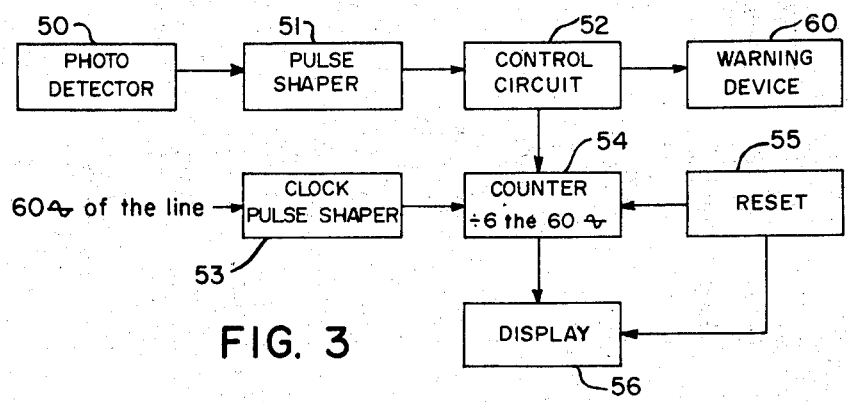
FIG. 3 is a block diagram of an embodiment in accordance with the present invention.

FIG. 3 is a block diagram of an electronic circuit which is adapted to measure the time elapsed while the gas-trapping object is immersed in the fluid. Photodetector 50 consists of lamps 10 and 11 and photoresistors 20 and 21 as shown in FIGS. 1 and 2 in a circuit such as that depicted in FIG. 4. When either light beam is interrupted, as would happen if an object were to enter the fluid or float on its surface, a pulse is fed from photodetector circuit 50 to the pulse shaper 51. Pulse shaper 51 merely modifies the pulse fed for the photodetector circuit 50 in that the output of pulse shaper 51 consists of square pulses of either the same or reverse polarity as the input pulses. These square pulses are fed into control circuit 52 which starts or stops a counter 54 and optionally activates warning device 60. Control circuit 52 feeds a modified square pulse from that received from pulse shaper 51. The pulse is of the appropriate polarity to start or stop counter 54, and the pulse is of sufficient length so that if the gas-trapping object flips over and interrupts the light beam more than once before sinking, the second pulse generated by the pulse shaper will be ignored. The length of the output pulse from control circuit 52 is easily adjusted. Optional warning device 60 could consist of a sound or light emitting mechanism to either operate while the counter is activated or immediately when the gas trapping object floats to the surface of the fluid.

Clock pulse shaper 53 merely changes the 60 Hertz alternating line voltage into a 60 cycle square wave, and feeds these square wave pulses to counter 54. Counter 54 receives an input from control circuit 52 which either starts or stops its counting. Counter 54 is designed to output every 6th pulse to display 56. Hence, while counter 54 is operating, display 56 digitally records pulses received at intervals of 1/10 of a second. Since counter 54 operates only while the gas-trapping object is immersed in the fluid, display 56 digitally displays the interval of time elapsed from the time that the object enters the fluid until it floats to the surface of the fluid. Display 56 is an appropriate integrated circuit capable of displaying digitally the output of counter 54. Reset circuit 55 consists of a push button which, when depressed, automatically resets counter 54 and display 56 to zero.

Figure 4:
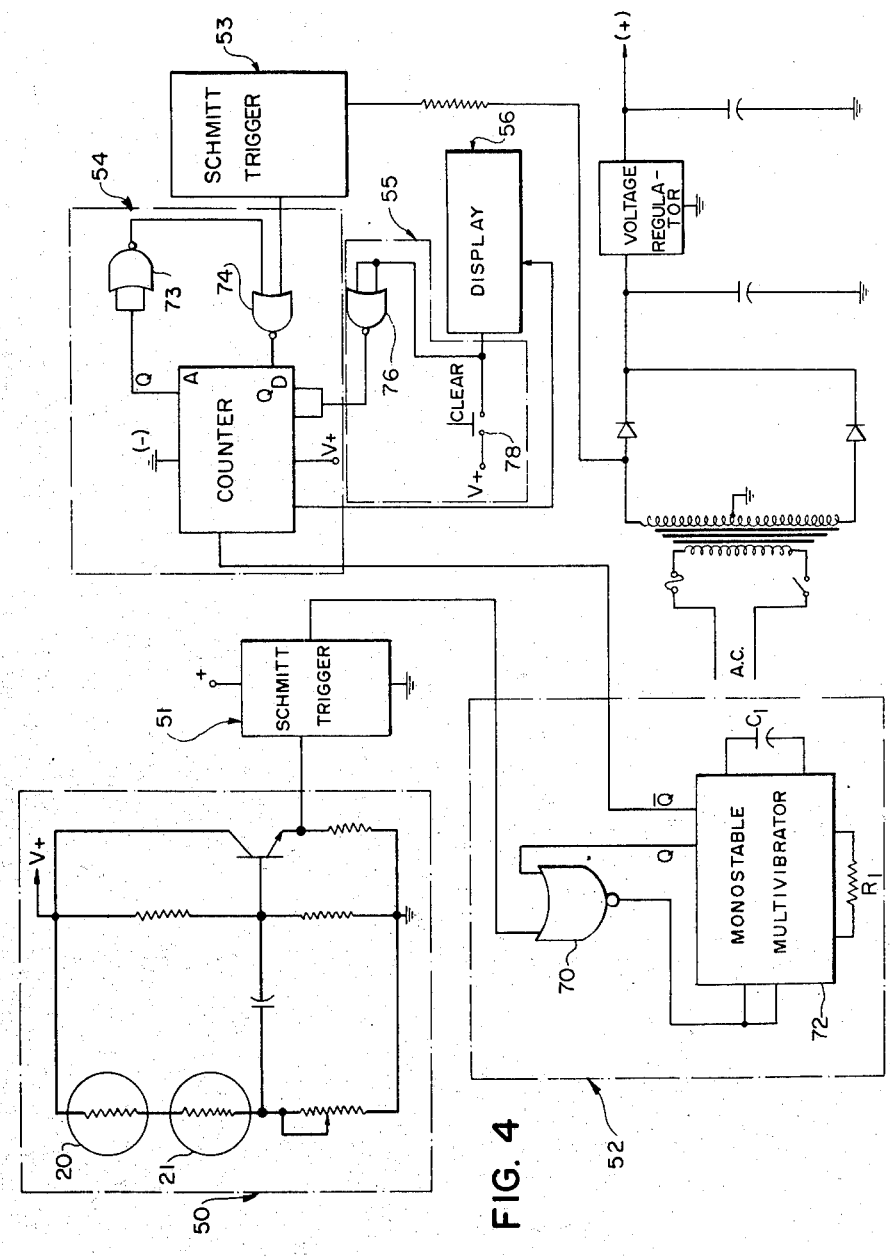
FIG. 4 is a schematic diagram of an embodiment in accordance with the present invention.

Referring now to FIG. 4, photodetector circuit 50 could be implemented as shown. While the light beam is uninterrupted, the transistor is biased into saturation so that the input to pulse shaper circuit 51 is at a reference potential. In the embodiment shown in FIG. 4, the reference potential will be of a positive polarity and the remaining circuitry is adapted to be compatible with this positive reference polarity. However, by changing the transistor type, a reference potential of the opposite polarity could be derived. It should be understood that the scope of the present invention contemplates both situations. When an object interrupts either light beam, the photoresistors change in value so as to bias the transistor into cutoff thus producing a negative going pulse which is fed to the pulse shaper 51. Photodetector circuit 50 contains an anti-heat drift circuit to compensate for voltage changes due to heat caused by the lamps. Pulse shaper 51 is an integrated circuit which merely changes the input pulse from photodetector circuit 50 to a well defined square pulse of appropriate polarity to activate control circuit 52. A possible integrated circuit for the pulse shaper 51 is a Schmidt Trigger No. SN5413N manufactured by Texas Instruments.

Control circuit 52 could be implemented as shown in FIG. 4. This circuit consists of a NOR gate 70 and a monostable multivibrator 72. When an object breaks one or both light beams 12 or 14 as shown in FIG. 2, a low level logic pulse is fed from pulse shaper 51 to one input of gate 70. If monostable multivibrator 72 is in its stable state, a low level logic voltage is applied to the second input of gate 70. This low level voltage will ready gate 70 only if monostable multivibrator 72 is ready to receive a pulse from gate 70. If both inputs of gate 70 are conditioned with low level logic voltages, gate 70 produces a high level logic voltage which is fed to monostable multivibrator 72 which changes state. Monostable multivibrator 72 changes state for a predetermined time period depending on the value of capacitor Cl and resistor Rl. This time period is made long enough to filter out any additional pulses coming from the pulse shaper 51 due to the gas-trapping object flipping over upon entry into the fluid.

Counter 54 is composed of an integrated circuit, such as Type SN7492A manufactured by Texas Instruments, and NOR gates 73 and 74, as shown in FIG. 4. When the light beam is interrupted, a low pulse is fed from control circuit 52 to activate counter 54. Substantially square clock pulses having a 60 cycle repetition rate are also fed to counter 54 from clock pulse shaper 53. When activated, counter 54 feeds every sixth pulse to display 56, thus counting in tenths of seconds. Invertor gate 73 assures that the counter will count the clock pulses only when activated, since the output from NOR gate 74 is high when the counter is not activated by control circuit 52 and low when activated. Clock pulse shaper 53 merely changes the 60 hertz line voltage into 60 hertz square wave pulses. A typical device for this purpose would be a Schmidt Trigger No. SN7413N, manufactured by Texas Instruments. Reset circuit 55 is comprised on invertor gate 76 and push button 78. When depressed, push buttons 78 resets counter 45 and display 56 to zero. Display 56 numerically displays the number of pulses received from counter 54. This means it displays the reaction time in tenths of seconds. A typical display would be type TIL306, manufactured by Texas Instruments.

The embodiment described above is designed to operate on a 60 hertz line frequency. It should be understood that if a different line frequency is used, the counter 54 would be changed accordingly. For example, if a 50 cycle line frequency was used the counter would be changed to a divide by 5 counter.

What we claim as our invention is:

1. A circuit for electronically measuring and displaying a readout of elapsed time for a gas-trapping object saturated with a medium containing a first reactant to buoyantly rise within and break the surface of a fluid containing a second reactant at a predetermined concentration in a container due to the reaction of said first and second reactants to produce a gas following said gas-trapping object breaking said surface and sinking in the fluid, said circuit comprising:

a. photo-detector means for producing a start pulse when said gas-trapping object breaks said surface to sink in said fluid and a stop pulse when said gas-trapping object buoyantly rises and again breaks the surface of said fluid;

b. clock means for displaying said elapsed time between said start pulse and said stop pulse, said elapsed time being proportional to the concentration of said first reactant in said medium; and c. means for electrically connecting said clock means and said photo-detector means, said electrically connecting means including means for passing said stop pulse only if said stop pulse should be produced after a predetermined time period following said production of said start pulse.

2. A circuit for electronically measuring and displaying a readout of elapsed time for a gas-trapping object saturated with a medium containing a first reactant to buoyantly rise within and break the plane of the surface of a fluid containing a second reactant at a predetermined concentration in a container due to the reaction of said first and second reactants to produce a gas following said gas-trapping object having broken said plane and sunken in the fluid, said circuit comprising:

a. photo-detector means for producing a start pulse when said gas-trapping object breaks said plane to sink in said fluid and a stop pulse when said gas-trapping object buoyantly rises and again breaks said plane of said fluid;

b. clock means for displaying said elapsed time between said start pulse and said stop pulse, said elapsed time being of at least a predetermined duration thereby to be proportional to the concentration of said first reactant in said medium; and, c. means for electrically connecting said clock means and said photo-detector means.

3. A circuit according to claim 2 wherein said photo-detector means includes at least one light source and photo-resistor, said light source and photo-resistor being paired and arranged on opposite sides of said container in a plane of the surface of said fluid.

4. A circuit according to claim 2 wherein said photo-detector means includes two light sources and photo-resistors, each said light source and photo-resistor being paired and arranged on opposite sides of said container in a plane of the surface of said fluid, said pairs being substantially orthogonally positioned with respect to one another.

5. A circuit according to claim 4 wherein said photo-detector means includes switch means, and said photo-resistors of said light source-photo-resistor pairs connected to said switch means, said switch means producing a pulse each time said gas-trapping object passes between at least one of said light source-photo-resistor pairs.

6. A circuit for electronically measuring and displaying a readout of elapsed time for a gas-trapping object saturated with a medium containing a first reactant to buoyantly rise within and break the surface of a fluid containing a second reactant at a predetermined concentration in a container due to the reaction of said first and second reactants to produce a gas following said gas-trapping object breaking said surface and sinking in the fluid, said circuit comprising:

a. photo-detector means for producing a start pulse when said gas-trapping object breaks said surface to sink in said fluid and a stop pulse when said gas-trapping object buoyantly rises and again breaks the surface of said fluid, said photo-detector means including
  1. two light sources,
  2. two photo-resistors, each said light source and photo-resistor being paired and arranged on opposite sides of said container in a plane of the surface of said fluid, said pairs being substantially orthogonally positioned with respect to one another, and
  3. switch means, said photo-resistors of said light source-photo-resistor pairs connected to said switch means, said switch means producing a pulse each time said gas-trapping object passes between at least one of said light source-photo-resistor pairs;

b. clock means for displaying said elapsed time between said start pulse and said stop pulse, said elapsed time being proportional to the concentration of said first reactant in said medium; and, c. means for electrically connecting said clock means and said photo-detector means, said means including
  1. pulse shaper means, said pulse shaper means producing a substantially square output pulse upon receipt of each said pulse from said switch means, and
  2. means connecting said pulse shaper means and said switch means.

7. A circuit according to claim 6 wherein said electrical connecting means further includes control circuit means connected to said pulse shaper, said control circuit producing said start pulse upon receipt of said substantially square output pulse and thereafter said stop pulse if and only if said control circuit means receives said next substantially square output pulse a predetermined time period after receipt of the preceding substantially square output pulse.

8. A circuit according to claim 7 wherein said clock means includes clock pulse shaper means, said clock pulse shaper means connected to means providing a substantially sinusoidal 60 hertz output signal for producing substantially square clock pulses having a 60 cycle repetition rate.

9. A circuit according to claim 8 wherein said clock pulse shaper means is a Schmidt trigger.

10. A circuit according to claim 8 wherein said clock means further includes electronic counting means, said electronic counting means being connected to said control circuit means and to said clock pulse shaper means, said electronic counting means starting its count upon receipt of said start pulse, stopping its count upon receipt of said stop pulse and, while counting said clock pulses, producing a count output pulse upon counting each sixth clock pulse, thereby producing count output pulses at intervals of 0.1 seconds.

11. A circuit according to claim 10 wherein said clock means further includes display means, said display means connected to said electronic counting means for displaying the count of the number of said count output pulses.

12. A circuit according to claim 11 wherein said display means is a light emitting diode display.

* * * * *

UNITED STATES PATENT AND TRADEMARK OFFICE
CERTIFICATE OF CORRECTION

PATENT NO. : 4,015,121
DATED : March 29, 1977
INVENTOR(S) : MARCEL GAGNON, MICHEL BARIL, FRANCOIS-GROS D'AILLON and CLAUDE SAVOIE It is certified that error appears in the above-identified patent and that said Letters Patent are hereby corrected as shown below:

Column 2, line 22, "oject" should be --object--.

Column 3, line 20, "for" should be --from--.

Column 4, line 17, the word --logic-- should be inserted after "level".

Signed and Sealed this fifth Day of July 1977

[SEAL]

Attest:

RUTH C. MASON
Attesting Officer

C. MARSHALL DANN
Commissioner of Patents and Trademarks